(12) United States Patent
Patton

(10) Patent No.: US 9,562,895 B2
(45) Date of Patent: Feb. 7, 2017

(54) ASSAY PARTICLES AND METHODS OF USE

(75) Inventor: Wayne F. Patton, Newton, MA (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 599 days.

(21) Appl. No.: 12/689,730

(22) Filed: Jan. 19, 2010

(65) Prior Publication Data

US 2010/0173315 A1  Jul. 8, 2010

Related U.S. Application Data

(62) Division of application No. 11/503,312, filed on Aug. 11, 2006, now abandoned.
(Continued)

(51) Int. Cl.
*G01N 33/543* (2006.01)
*C12Q 1/42* (2006.01)
(Continued)

(52) U.S. Cl.
CPC ........... *G01N 33/54313* (2013.01); *C12Q 1/42* (2013.01); *C12Q 1/485* (2013.01);
(Continued)

(58) Field of Classification Search
CPC ........ C04B 38/009; C04B 35/10; C04B 35/14; C04B 18/082; C04B 2235/528; C04B 35/62897; C04B 41/4584; C04B 14/24; C04B 2235/3232; C04B 2235/3427
(Continued)

(56) References Cited

U.S. PATENT DOCUMENTS

| | | |
|---|---|---|
| 4,568,649 A | 2/1986 | Bertoglio-Matte |
| 5,246,869 A | 9/1993 | Potter et al. |
| | (Continued) | |

FOREIGN PATENT DOCUMENTS

| | | |
|---|---|---|
| CN | 1381308 | 11/2002 |
| WO | WO 02/27318 | 4/2002 |
| | (Continued) | |

OTHER PUBLICATIONS

Caruso et al. "Multilayered Titania, Silica, Laponite Nanoparticle coatings on polystyrene colloidal templates and resulting inoganic hollow spheres" Chem. Mater. 2001, 13, 400-409.*
(Continued)

*Primary Examiner* — Mark Shibuya
*Assistant Examiner* — Pensee Do
(74) *Attorney, Agent, or Firm* — Fish & Richardson P.C.

(57) ABSTRACT

The invention provides assay particles useful, for example, for detecting analytes and binding molecule interactions. One type of assay particle includes a core portion encased by a shell portion, wherein the shell portion comprises an inorganic phosphor that binds selectively to a target molecule. Another type of an assay particle includes a core portion encased by a shell portion, and a coat portion covering the shell portion, wherein the coat portion comprises an inorganic phosphor that binds selectively to a target molecule. A further type of assay particle includes a core portion encased by a shell portion, and a coat portion covering the shell portion, wherein the coat portion comprises an inorganic phosphor and a target selective binding moiety, and wherein the assay particle is buoyant in aqueous media. An additional type of assay particle includes a core portion encased by a shell portion, and a coat portion covering the shell portion, wherein the shell portion comprises an inorganic phosphor and the coat portion comprises
(Continued)

a target selective binding moiety, and wherein the assay particle is buoyant in aqueous media. Also provided are kits and related methods.

60 Claims, 4 Drawing Sheets

Related U.S. Application Data

(60) Provisional application No. 60/707,492, filed on Aug. 11, 2005.

(51) Int. Cl.
  *C12Q 1/48* (2006.01)
  *G01N 33/542* (2006.01)
  *G01N 33/573* (2006.01)

(52) U.S. Cl.
  CPC ....... *G01N 33/542* (2013.01); *G01N 33/5432* (2013.01); *G01N 33/5436* (2013.01); *G01N 33/54306* (2013.01); *G01N 33/573* (2013.01); *G01N 2333/916* (2013.01); *G01N 2333/9121* (2013.01)

(58) Field of Classification Search
  USPC .................................................. 436/525, 518
  See application file for complete search history.

(56) References Cited

U.S. PATENT DOCUMENTS

| | | |
|---|---|---|
| 5,512,753 A | 4/1996 | Thomson et al. |
| 6,004,525 A | 12/1999 | Tani et al. |
| 6,045,777 A * | 4/2000 | Church et al. ............... 424/9.52 |
| 6,524,786 B1 | 2/2003 | Jessop |
| 6,537,829 B1 | 3/2003 | Zarling et al. |
| 6,614,723 B2 * | 9/2003 | Pearce et al. ................. 367/154 |
| 6,803,203 B1 | 10/2004 | Anderson et al. |
| 6,921,496 B2 | 7/2005 | Anderson et al. |
| 7,102,005 B2 | 9/2006 | Agnew et al. |
| 2001/0032963 A1 | 10/2001 | Kijima et al. |
| 2002/0042901 A1 | 4/2002 | Miyauchi et al. |
| 2003/0082237 A1 * | 5/2003 | Cha et al. .................... 424/490 |
| 2004/0180394 A1 | 9/2004 | Brandish et al. |
| 2004/0197819 A1 * | 10/2004 | Yang et al. .................... 435/7.1 |
| 2004/0249586 A1 | 12/2004 | Boge et al. |
| 2005/0106105 A1 * | 5/2005 | Gabe et al. .................... 424/9.5 |
| 2006/0105170 A1 | 5/2006 | Dobson et al. |
| 2006/0172339 A1 * | 8/2006 | Patton et al. ........ G01N 33/585 435/7.1 |
| 2007/0212542 A1 | 9/2007 | Guo et al. |

FOREIGN PATENT DOCUMENTS

| | | |
|---|---|---|
| WO | WO 02/074431 | 9/2002 |
| WO | WO 2007/022074 | 2/2007 |

OTHER PUBLICATIONS

Brandish et al., *Scintillation Proximity Assay of Inositol Phosphates in Cell Extracts: High-Throughput Measurement of G-Protein-Coupled Receptor Activation*, Anal Biochem. 313:311-8 (2003).

Bryant et al., *WGA-Coated Yttrium Oxide Beads Enable an Imaging-Based Adenosine 2a Receptor Binding Scintillation Proximity Assay Suitable for High Throughput Screening*, Assay Drug Dev Technol. 2:290-9 (2004).

Caruso, *Nanocasting and Nanocoating*, Top Curr Chem. 226:91-118 (2003).

Supplementary European Search Report in EP 06 78 9740 mailed Sep. 10, 2009, 11 pages.

Larsen et al., *Highly Selective Enrichment of Phosphorylated Peptides from Peptide Mixtures Using Titanium Dioxide Microcolumns*, Mol Cell Proteomics (2005) [Epub ahead of print].

Niesen et al., *Review: Deposition of Ceramic Thin Films at Low Temperatures from Aqueous Solutions*, J. Electroceram. 6:169-207 (2001).

Onda et al., *Wet Electrons at the H2O/TiO2(110) Surface*, Science 308:1154-1158 (2005).

International Search Report and Written Opinion in PCT/US06/31615, mailed Sep. 15, 2008.

Communication from European Patent Office; Application No. 06789740.5-2404; mailed Sep. 8, 2009; (11 pages).

Communication from European Patent Office; Application No. 06789740.5-2404; mailed Nov. 17, 2009; (1 page).

Communication from European Patent Office; Application No. 06789740.5-2404; mailed Jun. 17, 2010; (5 pages).

Canadian Office Action; Application No. 2618715; mailed Oct. 5, 2012; 2 pages.

Canadian Office Action; Application No. 2618715; mailed Jul. 17, 2013; 4 pages.

* cited by examiner

SEQUENCE LISTING

```
<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: laboratory-synthesized protein sequence

<400> SEQUENCE: 1

Glu Ala Ile Tyr Ala Ala Pro Phe Ala Lys Lys Lys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: laboratory-synthesized protein sequence

<400> SEQUENCE: 2

Pro Leu Ser Arg Thr Leu Ser Val Ser Ser
1               5                   10
```

ASSAY PARTICLES AND METHODS OF USE

This application is a divisional of and claims the benefit of priority under 35 U.S.C. §120 to U.S. application Ser. No. 11/503,312 having a filing date of Aug. 11, 2006, which claims the benefit of priority under 35 U.S.C. §119(e) of U.S. Application No. 60/707,492, filed Aug. 11, 2005. The disclosures of each of these applications are incorporated herein by reference in their entirety.

SEQUENCE LISTING

The document includes a sequence listing in electronic format submitted to the United States Patent and Trademark Office via the electronic filing system. The ASCII text file, which is incorporated-by-reference herein, is titled "10296-0074002.txt," was created on Aug. 11, 2016, and has a size of 775 bytes.

BACKGROUND

The scintillation proximity assay (SPA) is an approach for assay development and biochemical screening that allows rapid and sensitive measurement of molecular interactions in a homogeneous system, obviating the need for separation and washing steps. In theory, all that is required in the assay is mixing and measurement. The technology has proven useful in radiometric screening since its adoption in about 1992, with hundreds of PubMed literature references citing SPA applications to date. SPA is considered to be convenient, cost effective and safer than radioactive filter binding assays, providing fewer handling steps, no need for filters and scintillation cocktails as well as reduced disposal costs. The signal detection for SPA can be performed using any photomultiplier tube-based scintillation counter or CCD camera imager. SPA has enabled advances in high throughput screening, being both automation-friendly and requiring minimal hands-on involvement. It has been estimated that the assay provides a 30-fold increase in productivity relative to typical filtration assays.

Turning to the technical aspects of SPA, binding reactions can be assayed without the washing or filtration procedures normally used to separate bound from free fractions. Assays are typically performed using radioactive labels that emit electrons with only a short range (about 10 um) in water. When bound close to a solid scintillator surface by the binding reaction the radioactive labels are able to transfer electron energy to the scintillator to produce photons detectable with a scintillation counter. Electrons emitted from labeled molecules not bound close to the surface dissipate their energy in the medium and are not detected. The amount of light (photons) generated is proportional to the amount of radiolabeled molecules bound to the solid scintillant. Thus the bound fraction is detected specifically without separation of the solution from the support.

SPA beads are microscopic beads which contain a scintillant that can be stimulated to emit light. As is indicated above, this stimulation event only occurs when radiolabeled molecules of interest are bound to the surface of the bead, then blue light is emitted that can be detected on standard scintillation counters. Another type of SPA beads, often referred to as SPA imaging beads, emit red light that can be detected on standard CCD cameras. Assay plates coated with scintillant have also been used for SPA methods.

Further applications, formats, materials and procedures for performing SPA and SPA-like technologies are expected to contribute further to high throughput screening capability as well as to advances in bioanalytical and biomedical sciences.

SUMMARY

Figure 1:
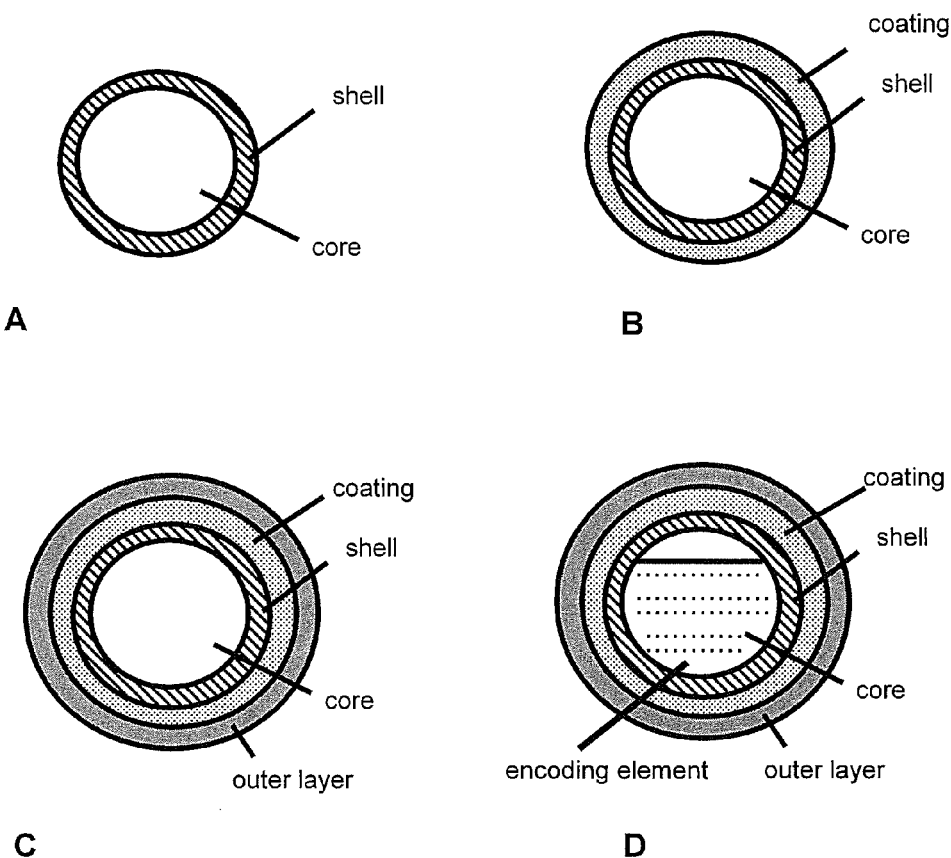
FIG. 1 shows exemplary assay particles encompassed within the technology described herein. The drawings exemplify cross-sections of assay particles having (A) a core and a shell portion; (B) core, shell and coating portions; (C) core, shell, coating and outer layer portions; and (D) a core portion containing an exemplary type of encoding element.

The invention provides assay particles useful, for example, for detecting analytes and molecular interactions. One type of assay particle includes a core portion encased by a shell portion, wherein the shell portion comprises an inorganic phosphor that binds selectively to a target molecule. Another type of an assay particle includes a core portion encased by a shell portion, and a coat portion covering the shell portion, wherein the coat portion comprises an inorganic phosphor that binds selectively to a target molecule. A further type of assay particle includes a core portion encased by a shell portion, and a coat portion covering the shell portion, wherein the coat portion comprises an inorganic phosphor and a target selective binding moiety, and wherein the assay particle is buoyant in aqueous media. An additional type of assay particle includes a core portion encased by a shell portion, and a coat portion covering the shell portion, wherein the shell portion comprises an inorganic phosphor and the coat portion comprises a target selective binding moiety, and wherein the assay particle is buoyant in aqueous media. In an embodiment, the core portion of an assay particle can include a material selected from the group of a gas, a liquid, a solid and a mixture thereof, such as a material selected from the group of air, organic solvent and organic polymer. In an embodiment, an assay particle can be buoyant in aqueous media. In an embodiment, the target molecule is a phosphorylated molecule. inorganic phosphor is selected from the group of rare-earth ion-doped yttrium oxide, rare-earth ion-doped zirconium oxide, rare-earth ion-doped yttrium oxysulfide and rare-earth ion-doped yttrium aluminum garnet. The rare-earth dopant can be selected from, for example, the group of terbium (III), europium (III), dysprosium (III), samarium (III), ruthenium (II), rhenium (I) and a combination thereof. In an embodiment, the assay particle has a density of less than 1 g/cm3. 1. In some embodiments, the target selective binding agent can be, for example, selected from the group of antibody, aptamer, protein A, protein G, streptavidin, avidin, captavidin, neutravidin, metal chelate, siderophore, lectin, and an oligonucleotide.

The invention provides methods for detecting a target molecule using an assay particle described herein. In one aspect, a method involves contacting a sample suspected of containing the target molecule with an assay particle, wherein (i) the target molecule comprises a moiety capable of emitting radiation, and (ii) the assay particle comprises a shell portion comprising an inorganic phosphor capable of binding selectively to target molecules; wherein binding of the target molecule to the inorganic phosphor produces a light signal, whereby the target molecule is detected.

DETAILED DESCRIPTION

The technology described herein provides assay particles and related methods and kits for detecting analytes and performing protein interaction and enzyme assays, such as protease, kinase, phosphatase, receptor binding, and molecular interaction assays, in scintillation and luminescence proximity assay formats, as well as fluorescence assay formats.

Assay beads have become an important tool for performing high throughput assays in biomedical research and drug development. Various commercial SPA methods involve using plastic beads (for example, polystyrene, polyvinyltoluene or polyethyleneimine) containing an organic scintillant, such as 2,4-diphenyloxazole (PPO) or anthracene. Other SPA methods use beads made from the inorganic scintillators yttrium silicate or yttrium oxide. Various inositol phosphates and phosphorylated lipids, most particularly sphingosine phosphate, have previously been detected and quantified by SPA using commercially available solid yttrium silicate and solid yttrium oxide particles (Brandish et al, 2003; 2004; Noremant et al, 2002).

The technology provided herein includes assay particles that can be used in proximity assays of various types, including SPA. One type of assay particle provided herein has a shell portion, which is made from an inorganic phosphor material, and which encases a core portion. The particular inorganic phosphor material used for this assay particle has the ability to bind to target molecules. As an example, the inorganic phosphor material can be a hydrated metal oxide, such as $TiO_2$, which can bind selectively to phosphorylated molecules. Exemplary constructions of such assay particles include $TiO_2$ formed into hollow microspheres (the shell) surrounding a core of air or another gas, and $TiO_2$ layered as a shell onto a polymer core. In either case, the resulting assay particle can have a low density relative to the assay solution, if desired. Another type of assay particle provided herein also has a shell and core, but further has a coating portion. The coating portion in this case contains an inorganic phosphor that has the ability to bind to target molecules. Carrying on with the $TiO_2$ example, an exemplary construction of an assay particle having a coating portion include a hollow microsphere (the shell and core) coated with $TiO_2$. A further type of assay particle provided herein has shell, core and coat portions, with either or both the shell and coat portions containing an inorganic phosphor and a target selective binding agent. This type of particle is composed of materials that allow it to be buoyant in aqueous media. Each of the assay particles can be relatively lightweight in comparison to typical metal oxide SPA beads, such as those referenced above, which are solid, and can be buoyant in aqueous media.

Therefore, the technology provides an assay particle, comprising a core portion encased by a shell portion, wherein the shell portion comprises an inorganic phosphor that binds selectively to a target molecule. In another embodiment, an assay particle of the invention includes a core portion encased by a shell portion, and a coat portion covering the shell portion, wherein the coat portion comprises an inorganic phosphor that binds selectively to a target molecule. In a further embodiment, an assay particle of the invention includes a core portion encased by a shell portion, and a coat portion covering the shell portion, wherein the coat portion comprises an inorganic phosphor and a target selective binding moiety, and wherein the assay particle is buoyant in aqueous media. In yet another embodiment, an assay particle of the invention includes a core portion encased by a shell portion, and a coat portion covering the shell portion, wherein the shell portion comprises and inorganic phosphor and the coat portion comprises a target selective binding moiety, and wherein the assay particle is buoyant in aqueous media.

The invention provides assay particles useful, for example, for detecting analytes and binding molecule interactions. One type of assay particle includes a core portion encased by a shell portion, wherein the shell portion comprises an inorganic phosphor that binds selectively to a target molecule. Another type of an assay particle includes a core portion encased by a shell portion, and a coat portion covering the shell portion, wherein the coat portion comprises an inorganic phosphor that binds selectively to a target molecule. A further type of assay particle includes a core portion encased by a shell portion, and a coat portion covering the shell portion, wherein the coat portion comprises an inorganic phosphor and a target selective binding moiety, and wherein the assay particle is buoyant in aqueous media. An additional type of assay particle includes a core portion encased by a shell portion, and a coat portion covering the shell portion, wherein the shell portion comprises an inorganic phosphor and the coat portion comprises a target selective binding moiety, and wherein the assay particle is buoyant in aqueous media. In an embodiment, the core portion of an assay particle can include a material selected from the group of a gas, a liquid, a solid and a mixture thereof, such as a material selected from the group of air, organic solvent and organic polymer. In an embodiment, an assay particle can be buoyant in aqueous media. In an embodiment, the target molecule is a phosphorylated molecule. The inorganic phosphor can be selected from the group of rare-earth ion-doped yttrium oxide, rare-earth ion-doped zirconium oxide, rare-earth ion-doped yttrium oxysulfide and rare-earth ion-doped yttrium aluminum garnet. The rare-earth dopant can be selected from, for example, the group of terbium (III), europium (III), dysprosium (III), samarium (III), ruthenium (II), rhenium (I) and a combination thereof. In an embodiment, the assay particle has a density of less than 1 g/cm3.

As used herein, the term "core portion" when used in reference to an assay particle of the invention means the innermost part of the particle, which is surrounded by a shell. The core portion can be composed of any substance containable within the shell portion of the assay particle, including one or more of a gas, solid, matrix, gel, colloid and liquid, and mixtures thereof. The composition of the core portion can be selected to impart certain physical properties to the assay particle, such as a particular magnetic, density or buoyancy property. Exemplary gases suitable for a core portion of an assay particle include air, nitrogen and oxygen. Exemplary liquids suitable for a core portion of an assay particle include oils, organic solvents, aqueous solutions and mixtures thereof. Exemplary solids and matrices, suitable for a core portion of an assay particle include organic materials such as cellulose, polyethyleneimine, dextran, agarose, polyacrylamide, polyvinyltoluene, Trisacryl, hydroxyalkyl methacrylate, poly(vinylacetate-co-ethylene), oxirane acrylate, polyethylene, polypropylene, poly(vinyl chloride), poly(methyl methacrylate), phenol resin, poly (vinylidene difluoride), poly(ethylene terephthalate), polyvinylpyrrolidone, polycarbonate and starch, and inorganic materials such as glass, ceramic, metal, glass, alumina, silica, zirconia, a ferromagnetic material and a paramagnetic material.

In an embodiment, an assay particle of the invention can be buoyant in an assay medium, typically an aqueous medium. An assay particle can have a low density relative to an assay medium or a density similar to an assay medium, for example, to render the assay particle buoyant in aqueous media. Therefore, a core portion can be selected to have a low density relative to one or both the shell portion and the coat portion (if present) of an assay particle, and also to have a density lower or similar to an assay medium. A core portion can therefore have a density of less than 1 $g/cm^3$, such as less than 0.5 $g/cm^3$ and 0.1 $g/cm^3$, although a more dense core portion can be used, for example, to obtain a buoyancy characteristic in a particular medium, such as a viscous medium. As a specific example of a core portion of an assay particle, described below is preparation of an assay particle having a gas core portion (Example 1). Assay particles having lower density than the aqueous medium, upon standing for a period of time, will float to the surface of the media, allowing their imaging above the assay container, which can reduce background in comparison to imaging particles in solution. In addition, larger particles having inorganic phosphor coatings become feasible to employ in SPA due to reduced settling of particles associated with the high density of inorganic particles or crystals. Larger particles or particles are readily imaged using less sophisticated CCD camera-based optical imaging techniques.

The term "shell portion" when used in reference to an assay particle of the invention means a skin or thickness of material surrounding or enveloping the core portion of the assay particle. The composition of the shell portion generally is selected to be compatible with the core portion of the assay particle. Thus, a relatively non-porous material is useful for the shell when the underlying core is a gas or liquid, whereas a non-porous or porous material can be suitable when the underlying core is, for example, a solid or matrix. The shell portion generally has a thickness of about 1 nm to about 500 nm, such as from about 1 nm to about 200 nm. A thickness can be selected, for example, based on the composition of the core, and to obtain an assay particle having a particular physical characteristic such as weight, strength, durability and the like. Exemplary materials for assay particle shells include glass, ceramic, metal, metal oxides, alumina, silica, and zirconia. Specific examples of shell materials are hollow glass and ceramic microspheres, which typically have relatively high strength to weight ratio. Commercially available glass and ceramic microspheres range in density from 0.16 to 0.7 $g/cm^3$, depending upon the specific product, with sizes typically ranging from 15 to 200 µm. Several varieties of bubbles and microspheres are available commercially from 3M™, including Scotchlite™ Glass Bubbles, Scotchlite™ Glass Bubbles Floated Series and Z-Light Spheres™ Ceramic microspheres. These micropheres range in size from 20 to 60 µm. Procedures for preparing microspheres and assay particles based on microspheres are described herein below.

The term "coat portion," when used in reference to an assay particle means a layer of material that covers the surface of the shell portion of the assay particle. A coat portion generally has a thickness of less than 3000 µm, such as less than 2000 µm and less than 1000 µm, depending on the coating material. The coat portion can be continuously or discontinuously present on the surface of the shell potion of an assay particle. The texture of the coat portion can vary from smooth to coarse, depending on the materials used. For example, the coat portion can have a surface of fine or coarse crystalline material, particulate material, proteinacious material, gel material, organic material and the like.

An assay particle described herein includes an "inorganic phosphor," present in the shell portion or the coat portion. As used herein, the term "phosphor" means a substance that emits light when excited by radiation, such as ultraviolet light, electron bombardment and electrical fields. A phosphor useful for an assay particle described herein is capable of converting radiation from a substance in a sample, such as an analyte or target molecule, into light energy that can be detected using a photomultiplier tube, CCD camera or the like. An inorganic phosphor useful for the assay particles described herein is typically capable of emitting light under conditions of a scintillation proximity assay (SPA).

An assay particle can also include a target selective binding agent, which is a substance that interacts with a target molecule but does not appreciably interact with other molecules in a sample. A target selective binding agent is useful for bringing an analyte or target molecule capable of emitting radiation into proximity with an inorganic phosphor, such that the inorganic phosphor absorbs radiation from the analyte or target molecule and produces a detectable signal. A target selective binding agent can bind with specificity to a general target species, such as a class of antibodies, a class of post-translationally modified proteins (for example, phosphomolecules and glycoproteins), and tags (for example, myc, polyhistidine and FLAG tags), or bind with specificity to a specific target species, such as a particular polypeptide. Exemplary target selective binding agents include an antibody, aptamer, protein A, protein G, streptavidin, avidin, captavidin, neutravidin, metal chelate, siderophore, lectin, and an oligonucleotide.

Examples of inorganic phosphors suitable for a shell or coating of an assay particle described herein include yttrium oxide, yttrium silicate, yttrium oxysulphide, yttrium aluminium gallium oxide, yttrium aluminium garnet, sodium yttrium fluoride, lanthanum fluoride, lanthanum oxysulphide, yttrium fluoride, yttrium gallate, gadolinium fluoride, barium yttrium fluoride, gadolinium oxysulphide, zinc silicate, zinc sulphide and yttrium vanadate. An inorganic phosphor can include a rare-earth ion dopant. Presence of a dopant in a hydrated metal oxide phosphor can render to the material luminescent or shift the emission maximum of the material. Non-limiting examples of metal oxides suitable for assay particles described herein include yttrium oxide, zirconium oxide, yttrium oxysulfide and yttrium aluminum garnet. Exemplary rare ion dopants include terbium (III), europium (III), dysprosium (III), samarium (III), ruthenium (II) and rhenium (I). A combination of one or more dopants also can be used. A variety of processes are suitable for applying an inorganic phosphor to a selected shell material. An inorganic phosphor layer can be deposited onto a ceramic or glass hollow microsphere, for example, by liquid-phase deposition, chemical bath deposition, successive ion layer adsorption and reaction (SILAR), electroless deposition, reactive sputtering, reactive evaporation, spray pyrolysis, track-etching, anodic oxidation, chemical vapor deposition, and sol-gel processing. The deposited layer can be crystalline, nanocrystalline, poorly crystallized or amorphous. In one embodiment, an assay particle contains an inorganic phosphor capable of selective binding to a target molecule. An example of such an inorganic phosphor is a hydroxylated metal oxide. One process for making a hydroxylated metal oxide layer is to form a crystalline metal oxide layer on a particle shell or core, and subsequently hydroxylate it. Hydroxylating can be achieved by incubation in an aqueous-based medium until sufficient hydroxylation has occurred to impart the phosphomolecule binding property. The ability of the hydroxylated metal oxide layer to bind phosphomolecules can be tested during the incubation, which generally occurs over a period of one hour to several months, depending on materials used. Deposition of a metal oxide can be achieved on an ion-by-ion or particle attachment basis. When an organic matrix or solid core is used, functionalization of an organic material, especially with sulfonate, hydroxyl, amine or carboxyl groups can improve depositing the inorganic phosphor.

An inorganic phosphor containing a hydrated metal oxide can be deposited onto a core or shell by low-temperature synthesis of thin films through direct deposition from aqueous-based solutions (see for example Niesen and De Guire, 2001) as well as alternative solvents, such as 2-propanol and blends of acetic acid, acetone and water. When an organic material is used for the core or shell portion, a solvent is selected to avoid damaging the organic material. For example, deposition of a hydrated metal oxide onto an organic material can occur near ambient temperature and in an aqueous-based medium. Without wishing to be bound by theory, it appears that heterogeneous nucleation is required for effective coating with hydrated metal oxides. Under certain circumstances, homogenous nucleation of supersaturated precursor metal ion solutions predominates and precipitation results. Under other conditions, the precursors form a metastable solution with very low reaction rate. Heterogeneous nucleation occurs at intermediate conditions between the metastable and supersaturated states. Often, reaction conditions can be adjusted to maintain purely heterogeneous nucleation and lessen homogeneous deposition, which can result in unwanted excessive deposition on the core or shell. Reaction conditions can be defined for a variety of suitable starting materials by construction of a phase diagram of the starting material concentration versus pH for a given temperature. Once the reaction conditions for heterogeneous nucleation are identified, the core (with or without a shell) is incubated in the reaction solution for a period of about 0.5 to 260 hours. The diameter of the coating gradually increases throughout the deposition time course. Incubation time is usually adjusted to achieve layer thicknesses that are 200 nm or less, as thicker layers may have a tendency to peel off the substrate after deposition. Particle sizes in the coatings typically range from a few nanometers to a few tens of nanometers. Optionally, inclusion of a surfactant, into the reaction solution, while suppressing the growth of crystals somewhat, also reduces the propensity of cracking or crazing, thus making a more durable coating. Exemplary surfactants that can be included in a reaction mixture include sodium dodecyl sulfate, lithium dodecyl sulfate, sodium bis-2-ethylhexylsulphosuccinate, sodium cholate, perfluordecyl bromide, cetyltrimethylammonium bromide, didodecylamonium bromide, Triton X-100, polyoxyethylene 10-oleyl ether, polyoxyethylene-10-dodecyl ether, N,N-dimethyldodecylamine-N-oxide, Brij 35, Tween-20, Tween-80, sorbitan monooleate, lecithin, diacylphosphatidylcholine, sucrose monolaurate and sucrose dilaurate. Deposition of the hydrated metal oxides can occur more readily upon hydrophilic materials, in comparison to hydrophobic materials.

Metal oxide or hydroxide coatings also be formed through the ligand-exchange (hydrolysis) equilibrium reaction of metal-fluoro complex ionic species and a fluoride consumption reaction using boric acid or aluminum metal (Niesen and De Guire, 2001). With the technique, coatings can be formed on a variety of organic cores and shells by immersion into the reaction solution. Multicomponent layers containing several metals (eg europium-doped yttrium oxide phosphor, yttrium oxysulfide phosphor, europium-doped spinel phosphor, europium-doped gadolinium oxide phosphor, europium-doped zirconia phosphor) also can be produced (Niesen and De Guire, 2001).

A metal oxide inorganic phosphor can also be coated onto a ceramic core or shell by mixing of metal oxide powder with a solution containing a binder, such as polyvinyl alcohol, polyethylene glycol, polyethyleneimine, poly(dimethylsiloxane), hydroxypropylcellose or polyacrylamide. Further well known deposition methods include reactive sputtering, reactive evaporation, spray pyrolysis, track-etching, anodic oxidation, cold-pressed molding, chemical vapor deposition and sol-gel processing. In general, these methods involve heating at temperatures above 400 degrees centigrade, to obtain sufficient crystallinity.

A metal oxide inorganic phosphor shell or coating portion of an assay particle can have a variety of textures, for example, the surface can be nano-porous, include ultrafine crystallites or be poorly crystallized. When it is desired for the inorganic phosphor to be capable of binding to phosphorylated molecules, the metal oxide surface contains hydroxide groups. Nevertheless, processes for preparing metal oxide coatings that result in reduced hydroxylation of the metal oxide surface can be used (for example, sintering), so long as the hydroxylated surface is regenerated after process. Hydroxyl groups can be regenerated, for example, by incubating the metal oxides in an aqueous environment.

Optimal interaction of phosphorylated molecules with inorganic phosphor scintillants depends upon the interaction between the hydrated oxide and the phosphate ion. In aqueous-based media the predominant surface functional group on metal oxides is the hydroxyl group. Without wishing to be bound by theory, it appears that at the proper pH value the surface hydroxyl groups are, in one embodiment, polarized and electrically charged to allow interaction with phosphorylated molecules. The oxide surface adsorbs and/or desorbs protons from solution, thus influencing the surface charge. This induces electrostatic effects in the vicinity of the charged surface, which directly impacts the capacity of the material for sorption of different ionic species from the aqueous-based media. At low pH values the surface charge becomes positive, while at high pH values it becomes negative. The pH value at which the particles possess no surface charge is referred to as the isoelectric point or pH of zero zeta potential. The loss or gain of protons is commonly considered as an acid-base reaction at the metal oxide surface. A variety of different surface hydroxyl groups can be present on a metal oxide surface. When a surface hydroxyl group is coordinated to a single metal atom, it is referred to as a singly coordinated or terminal hydroxyl group, whereas if the hydroxyl group is coordinated to two, three or four metal atoms, it is referred to as a bridging hydroxyl group. For iron oxides, the surface hydroxyl groups may be coordinated to one, two or even three underlying metal atoms. It is also possible for two surface hydroxyl groups to be bound to a single metal atom. The configurations of the different types of surface groups depend upon the structure of the oxide and the crystal face being examined, with different surface groups likely to display different chemical properties. Not all of the different types of surface groups are active in the titratable pH-range required for capture of phosphorylated molecules. Overall, adsorption of phosphorylated molecules is governed by a set of complex formation reactions between the dissolved phosphorylated solute and the titratable surface functional groups of the hydrated metal oxide surface. The interface between metal oxide and water is surprisingly complex, involving what has been dubbed "wet-electron" states (Onda et al, 2005). Despite this complexity, the inventor has determined that certain base materials for inorganic phosphors, specifically yttrium oxide and yttrium aluminum garnet, when hydrated, display specific, high affinity for phosphorylated compounds. In the case of titania surfaces, protonation and consequently positive charge attributes are achieved below the material's isoelectric point of approximately 6.0. Other metal oxide surfaces differ in the isoelectric point that is conducive to the generation of a proper surface for affinity capture of phosphorylated molecules. For example, highly hydrated zirconia possesses an isoelectric point of 8.2, while hematite, yttrium oxide, and gibbsite possess isoelectric point values of 7.5, 8.5, and 10.0, respectively. Inclusion of certain alkali metals in the media can shift the isoelectric point of hydrated metal oxide particles to higher pH values, as observed with rutile particles incubated with barium, calcium or magnesium salts. It is likely this is due to the precipitation of hydrous metal oxides onto the surface of the particles. Pure silica has an isoelectric point value of roughly 1.8, rendering the material unsatisfactory for the present methods and systems. However, the coating of silica with an appropriate hydrated metal oxide can provide a usable surface for binding phosphorylated molecules. It should also be noted that the isoelectric point of hydrated metal oxides depends somewhat upon the preparation method, trace impurities and the degree of hydration, among other factors. Overall, metal oxides of the general formula $Me_2O_3$ tend to have isoelectric point values of about 9.0, regardless of the metal ion incorporated in the structure. On the other hand metal oxides of the general formula $MeO_2$ display isoelectric point values that increase with the ionic radius of the metal atom and when the electronegativity of the metal atom decreases. Collectively all these factors can be valuable in optimizing and fine-tuning affinity-based detection of phosphorylated molecules using SPA.

The isoelectric point of the hydrated metal oxide effectively establishes an upper limit for the pH of binding buffers employed in affinity-based detection of phosphorylated molecules. When using particles comprising amorphous or weakly crystallized hydrated metal oxide, strongly acidic (pH<3.0) and strongly basic (pH>11.0) solutions are typically avoided due to chemical instability of the hydrated metal oxide surface under these conditions.

Assay particles can also be prepared using layered precursor deposition on sacrificial organic colloidal core particles. The organic template is used for controlled structuring of inorganic materials by nanocasting or nanocoating (Caruso, F. (2003); Caruso, R (2003)). The difference between the two techniques is that casting is a filling of the porous structure of the organic material, while coating results in a layer of the inorganic substance on the polymer structure. One approach to generating assay particles uses a layer-by-layer assembly process for the creation of coated particles (core-shell colloids) which are subsequently converted to hollow inorganic particles. Sacrificial core template particles are coated with multiple layers of preformed inorganic nanoparticles, or inorganic molecular precursors, and oppositely charged polyelectrolyte, using electrostatic attraction for construction of the layers on the particles. Calcination of the core-shell nanocomposite particles yields hollow inorganic particles of defined size and composition. The wall thickness can be controlled with nanoscale precision through the number of layers formed on the organic particles.

As is described herein, certain inorganic phosphors have the ability to bind selectively to target molecules. Therefore, in one embodiment, an assay particle of the invention includes an inorganic phosphor capable of binding selectively to a target molecule. A target specific binding agent can be used with an inorganic phosphor capable of binding to a target molecule when binding of additional or different target molecules to an assay particle is desired. One or more target selective binding agents can be present in one or both the coat portion of the assay particle and an outer layer on the coat portion. The term "outer layer" as used herein means a film, covering or deposition of a material onto the surface of the coat portion of an assay particle. The outer layer can be a continuous or discontinuous coating, film or deposition containing the target selective binding agent.

An assay particle can have a shape and size suited for its use. Typical assay particle shapes include spherical, cylindrical and irregular shapes. An assay particle described herein generally has a size of about 0.1 to about 10,000 um, such as about 1 μm to about 2000 um, about 1.5 to about 500 μm in size, and about 10 μm to about 100 μm in size. In one aspect, the technology described herein provides assay particles of size sufficiently small for dispensing in micro- or nanoliter volumes. The particular size selected will depend on equipment used for microdispensing, for example, for dispensing into 96-, 384- and 1536-well plates.

An assay particle described herein can also contain an "encoding element" that contains or imparts information, such as information about the particle, a set of particles, a sample, an analyte, a target selective binding agent and the like. The encoding element can be a physical element such as a radio frequency identifier, holographic or other identifier, or a chemical element such as one or more luminescent materials, for example, fluorophors and mixtures thereof, quantum dots and the like. A variety of well-recognized encoding systems are known to those skilled in the art, and can be adapted to the assay particles described herein. For example, Chandler et al. (U.S. Pat. No. 5,981,180) describes a particle-based system in which different bead types are encoded by mixtures of various proportions of two or more fluorescent dyes impregnated into polymer particles; Soini (U.S. Pat. No. 5,028,545) describes a particle-based multiplexed assay system that employs time-resolved fluorescence for particle identification; Fulwyler (U.S. Pat. No. 4,499,052) describes using beads distinguished by color and/or size; and Moon and Putnam (2004-0179267, 2004-0132205, 2004-0130786, 2004-0130761, 2004-0126875, 2004-0125424, and 2004-0075907) describe particles encoded by holographic barcodes. Such encoding elements can be located in any portion of the assay particle, including the shell portion, coating portion and outer layer. Use of encoding elements in assay particles described herein can be useful for performed multiplexed assays. Therefore, provided by the technology are multiplexed assays using assay particles of the invention. In these assays, a plurality of differently encoded assay particles is simultaneously assayed in a method described herein.

As a specific example, one type of assay particle of the invention is an encoded particle (i.e., a particle containing an encoding element) that has an inorganic phosphor deposited on its surface. A plurality of assay particles with different encoding elements can be used for measuring different analytes. For example, particles can be dyed with differing concentrations of two fluorophores to generate distinct particle sets, as is performed with Luminex beads. Each bead set is coated with a layer of inorganic phosphor and then a target specific binding agent specific for one particular analyte. The amount of captured analyte is detected based upon the magnitude of the scintillation signal of the inorganic phosphor coating, which is in direct proportion to the amount of analyte bound. The identity of the analyte is determined from the characteristic fluorescence properties of the core particle itself, as determined based upon color ratios. As another example, it is possible to classify the assay particles based upon a variety of other optical properties, such as their size or shape. As a further example, an organic solvent containing different ratios of fluorophore can be entrapped in inorganic phosphor coated assay particles to achieve similar objectives.

An assay particle as described herein can be prepared using a variety of known methods, which will vary depending on the particular materials selected for the core, shell and optional coat portions of the assay particle. In some cases a core will be prepared and encased within a shell, while in other cases the shell and core portions will form in the same process. For example, formation of a shell portion which is a glass microsphere will inherently result in formation of a core portion that is typically a gas.

In one embodiment, the shell and core of the assay particle are the body and inside of a hollow microsphere, respectively. Microspheres also can be synthesized by well-known techniques such as emulsion-ion extraction techniques, sol-emulsion-gel synthesis, or emulsion templating. The microspheres can be coated with an inorganic phosphor, as is described in detail herein, or can be generated directly from an inorganic phosphor. Commercial microspheres, such as those made from glass and ceramic, also can be used to form an assay particle of the invention. For crude microspheres, a variety of methods, such as physical screen separations, are suitable for further sizing the material, if desired.

The technology provided herein includes methods for detecting analytes and assaying enzyme activities. The methods are applicable to SPA assays, fluorescence resonance energy transfer assays, fluorescence polarization assays and other formats that involve the generation of a light signal upon binding of a molecule having a moiety capable of emitting radiation to an assay particle having an inorganic phosphor surface.

In one embodiment, the technology described herein provides a method for detecting a target molecule. The method involves contacting a sample suspected of containing the target molecule with an assay particle, wherein (i) the target molecule comprises a moiety capable of emitting radiation, and (ii) the assay particle comprises a shell portion comprising an inorganic phosphor capable of binding selectively to target molecules, wherein binding of the target molecule to the inorganic phosphor produces a light signal, whereby the target molecule is detected.

In another embodiment, a method for detecting a target molecule involves contacting a sample suspected of containing the target molecule with an assay particle, wherein (i) the target molecule comprises a moiety capable of emitting radiation, and (ii) the assay particle comprises a coat portion comprising an inorganic phosphor capable of binding selectively to target molecules; wherein binding of the target molecule to the inorganic phosphor produces a light signal, whereby the target molecule is detected.

In a further embodiment, a method for detecting a target molecule involves contacting a sample suspected of containing the target molecule with an assay particle, wherein (i) the target molecule comprises a moiety capable of emitting radiation, and (ii) the assay particle comprises a coat portion comprising an inorganic phosphor and a target selective binding agent, and is buoyant in aqueous media; wherein binding of the target molecule to the target selective binding agent activates the inorganic phosphor to produce a light signal, whereby the target molecule is detected.

As used herein the term "moiety capable of emitted radiation" means a chemical label or modification that emits radiation sufficient to activate an inorganic phosphor to emit a light signal. Non-limiting examples of such moieties include radioactive labels and luminescent labels such as fluorescent labels, phosphorescent labels, and chemilluminescent labels. Exemplary radioactive labels include $^{3}H$, $^{125}I$, $^{14}C$, $^{35}S$ $^{32}P$, $^{55}Fe$, $^{86}Rb$, $^{109}Cd$ and $^{51}Cr$ and $^{33}P$. Exemplary luminescent labels include fluorescent labels such as cyanine-5 (PerkinElmer), cyanine-3 (PerkinElmer, AlexaFluor 647 (Invitrogen), Quasar 670 (Bioserach Technologies), DY 630 (Dyomics), HiLyte Fluor (Anaspec) or various lanthanide chelates. A variety of fluorescent labels are described, for example, in Handbook of Fluorescent Probes and Research Products, Ninth Edition by Dr. Richard P. Haugland (Molecular Probes, 2003).

A variety of samples can be used for carrying out the methods described herein. A sample can, for example, be a biological sample, environmental sample, experimental sample, diagnostic sample, or any other type of sample that contains or is suspected to contain a target molecule of interest. In a biological context, a sample can be prepared from or include biological fluids, whole organisms, organs, tissues, cells, microorganisms, culture supernatants, subcellular organelles, protein complexes, individual proteins, recombinant proteins, fusion proteins, viruses, viral particles, peptides and amino acids. A sample can be processed to preserve or stabilize molecules of interest, such as enzymes and phosphorylated molecules. Methods for preserving the integrity of molecules in a sample are well known to those skilled in the art. Such methods include the use of appropriate buffers and/or inhibitors, including nuclease, protease and phosphatase inhibitors that preserve or minimize changes in the molecules in the sample. Such inhibitors include, for example, chelators such as ethylenediamne tetraacetic acid (EDTA), ethylene glycol bis(ρ-aminoethyl ether)N,N,N$^1$,N$^1$-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Appropriate buffers and conditions for allowing selective interactions between molecules are well known to those skilled in the art and can be varied depending, for example, on the type of molecule in the sample to be characterized (see, for example, Ausubel et al., Current Protocols in Molecular Biology (Supplement 47), John Wiley & Sons, New York (1999); Harlow and Lane, Using Antibodies: A Laboratory Manual, Cold Spring Harbor Press (1999); Tietz Textbook of Clinical Chemistry, 3rd ed., Burtis and Ashwood, eds., W.B. Saunders, Philadelphia, (1999)).

In an embodiment, the assay particles provided herein have shell or coat portions having a surface of inorganic phosphor capable of binding selectively to target molecules. In another embodiment, an assay particle of the invention includes an inorganic phosphor and a target selective binding agent. In a particular embodiment, the shell or coat portions include a hydrated metal oxide capable of binding to phosphorylated molecules. A specific example of such a metal oxide is titanium dioxide, as is described in Example 2. The ability of an inorganic phosphor to bind to a target molecule, such as a molecule that has been phosphorylated or otherwise modified, can be tested empirically. Therefore, the technology described herein provides methods for detecting phosphorylated molecules and methods for assaying enzymes. Exemplary enzymes that can be assayed based on levels of target molecules or substrates in a sample include enzymes that alter phosphorylation states of their substrates, for example, kinases and phosphatases, and enzymes that catalyze cyclization and decyclyzation of nucleotide monophosphates, such as cyclases and phosphodiesterases. The methods described herein are applicable to assaying a variety of target molecules, protein interactions, enzyme and receptor activities and the like.

Figure 3:
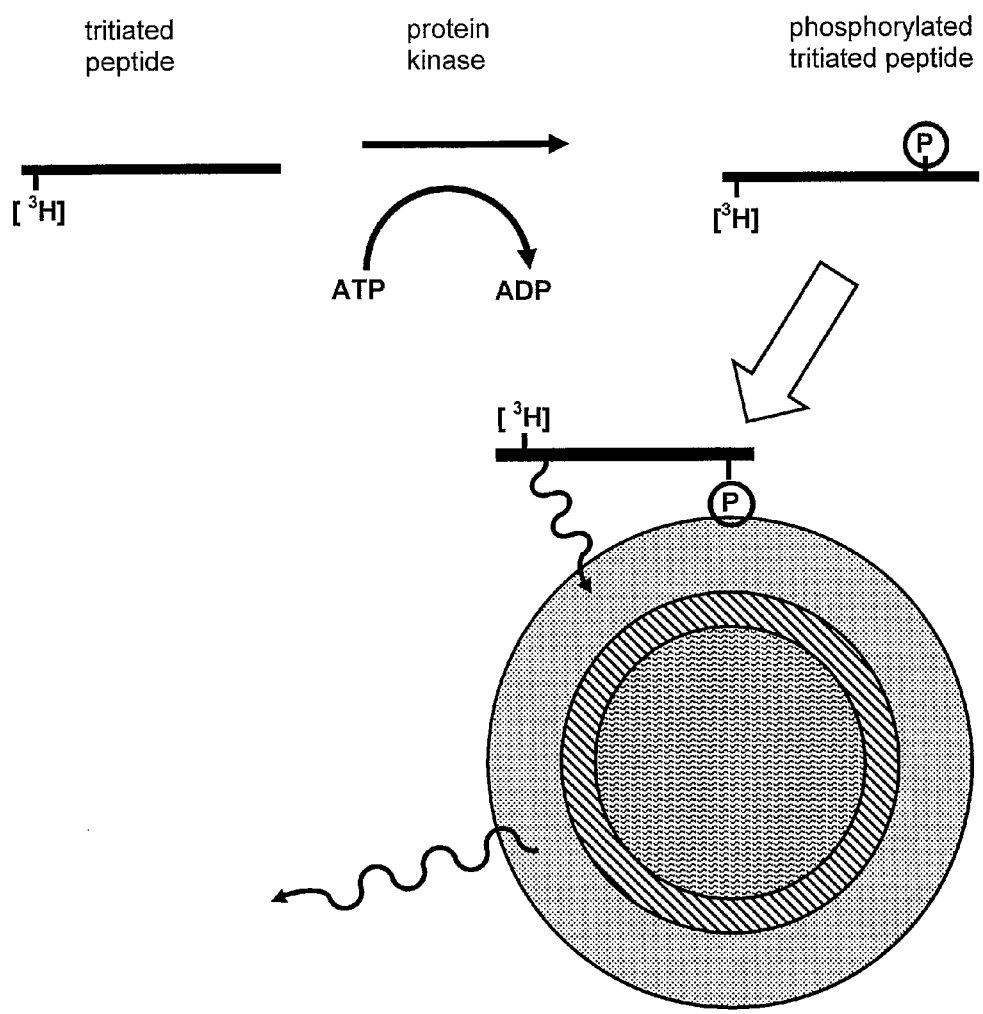
FIG. 3 shows a schematic diagram depicting an exemplary homogenous protein kinase scintillation proximity assay using a tritiated peptide substrate and an air-filled glass assay particle coated with an inorganic phosphor that binds selectively to phosphorylated molecules, according to an embodiment of the technology described herein.

An example of a protein kinase SPA assay is depicted in FIG. 3. In this example, a protein kinase present in the sample phosphorylates a substrate peptide. The substrate peptide contains a tritium label, which emits radiation whether or not it is phosphorylated. A substrate peptide that becomes phosphorylated will have an affinity for an assay particle coated with an inorganic phosphor that binds selectively to phosphorylated molecules, such as europium-doped yttrium oxide. A phosphorylated substrate peptide that binds to an assay particle will activate the particle to produce a light signal. This activation occurs because the tritium label emits a beta particle(s) that are in turn absorbed by the inorganic phosphor on the assay particle. As a result of absorbing such radiation, the inorganic phosphor emits a photon of light. In the case of europium-doped yttrium oxide, the light is emitted at 615 nm and correlates with the amount of phosphorylated peptide. The light signal is detectable using a variety of devices, such as scintillation counters and CCD camera imagers.

Figure 4:
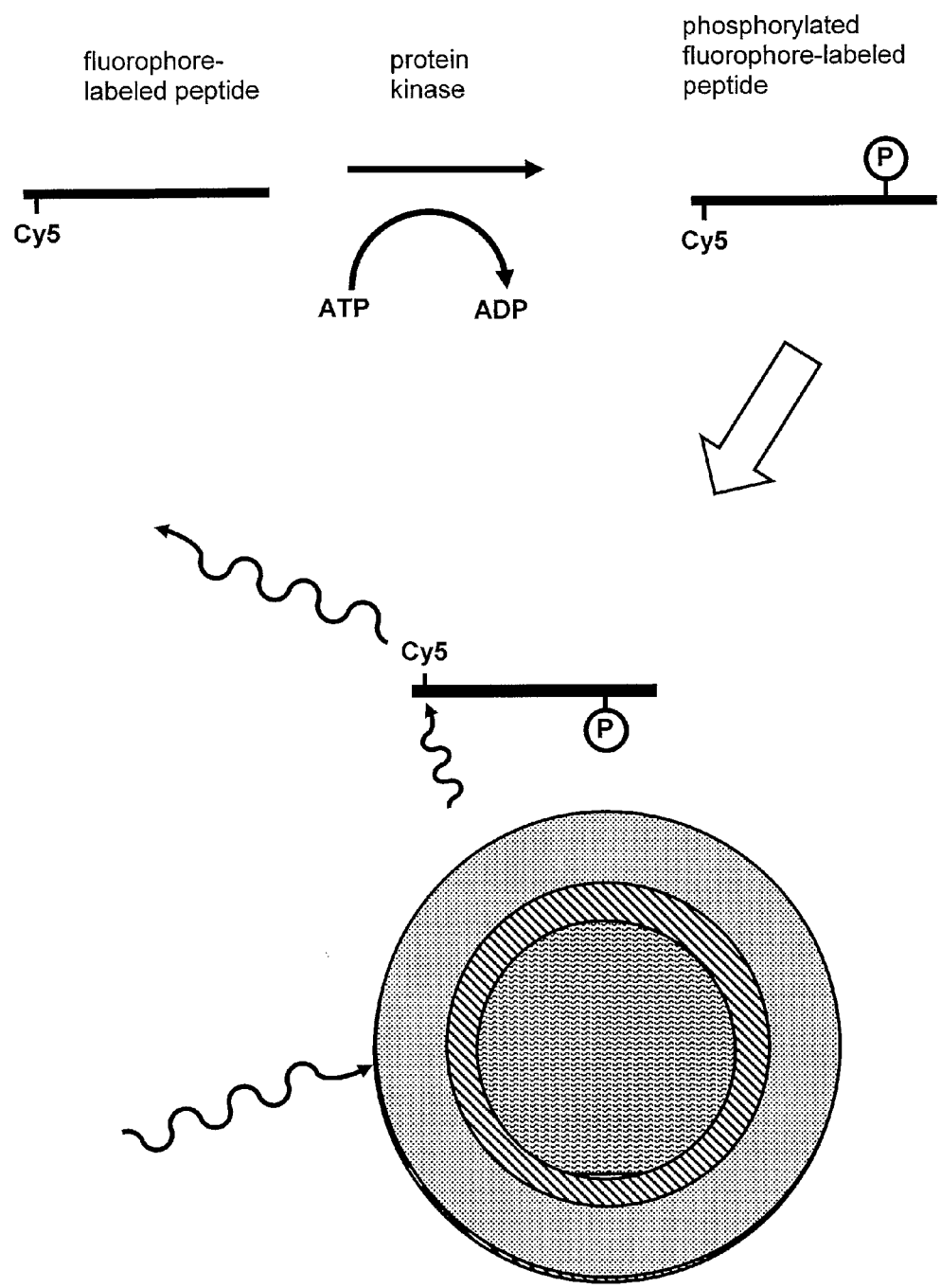
FIG. 4 is a schematic diagram of an exemplary homogenous protein kinase time-resolved fluorescence assay using a cyanine 5 dye-labeled peptide substrate and an air-filled glass assay particle coated with an inorganic phosphor that binds selectively to phosphorylated molecules, according to an embodiment of the technology described herein.

Another example of a protein kinase SPA assay is depicted in FIG. 4. The depicted format involves using time-resolved fluorescence to detect phosphorylated substrate. In the case of homogenous time-resolved fluorescence assays, the energy donor is the rare earth dopant in the inorganic phosphor, rather than radioactivity. The energy acceptor is a fluorophore whose excitation profile overlaps the emission profile of the dopant in the inorganic phosphor. Binding events are detected as emission of the longer wavelength fluorophore upon excitation of the shorter wavelength emitting phosphor with mid-range ultraviolet radiation. In this example, a protein kinase present in the sample phosphorylates a substrate peptide. The substrate peptide contains a cyanine 5 dye label, which can be excited by light to emit radiation. A substrate peptide that becomes phosphorylated will have an affinity for an assay particle coated with an inorganic phosphor that binds selectively to phosphorylated molecules, such as europium-doped yttrium oxide. Upon illumination with short wavelength UV light (~337 nm) fluorescence resonance energy transfer occurs between the inorganic phosphor coating and the cyanine 5 dye label, resulting in long-lived, 665-nm photon emission that correlates with the amount of phosphorylated peptide product formed. Fluorescence resonance energy transfer occurs if the cyanine 5 dye label on the substrate peptide is in close proximity with the inorganic phosphor. Binding of the substrate peptide to the assay particle brings it into sufficient proximity for energy transfer to occur, whereas substrate peptides unbound to the assay particle lack such proximity. The light signal is detectable using a variety of devices including fluorescence readers and CCD camera imagers.

In addition to SPA assays and fluorescence resonance energy transfer assays, fluorescence polarization assays also can be carried out using the methods described herein. To use a fluorescence polarization assay format, the assay particles are added to the kinase reaction along with a fluorescently-labeled peptide substrate. When phosphorylated by a protein kinase, the fluorophore-derivatized peptide substrate binds to the assay particle. This binding event results in the rotation of the fluorescent phosphorylated substrate being decreased, resulting in greater fluorescence polarization of the emitted light.

The invention provides methods for detecting a target molecule using an assay particle described herein. In one aspect, a method involves contacting a sample suspected of containing the target molecule with an assay particle, wherein (i) the target molecule comprises a moiety capable of emitting radiation, and (ii) the assay particle comprises a shell portion comprising an inorganic phosphor capable of binding selectively to target molecules; wherein binding of the target molecule to the inorganic phosphor produces a light signal, whereby the target molecule is detected. In another aspect, a method for detecting a target molecule involves contacting a sample suspected of containing the target molecule with an assay particle, wherein (i) the target molecule comprises a moiety capable of emitting radiation, and (ii) the assay particle comprises a coat portion comprising an inorganic phosphor capable of binding selectively to target molecules; wherein binding of the target molecule to the inorganic phosphor produces a light signal, whereby the target molecule is detected. In another aspect, a method for detecting a target molecule involves contacting a sample suspected of containing the target molecule with an assay particle, wherein (i) the target molecule comprises a moiety capable of emitting radiation, and (ii) the assay particle comprises a coat portion comprising an inorganic phosphor and a target selective binding agent, and is buoyant in aqueous media; wherein binding of the target molecule to the target selective binding agent activates the inorganic phosphor to produce a light signal, whereby the target molecule is detected. Similar methods can be used for an assay particle that includes a core portion encased by a shell portion, and a coat portion covering the shell portion, wherein the shell portion comprises an inorganic phosphor and the coat portion comprises a target selective binding moiety, and wherein the assay particle is buoyant in aqueous media.

The invention provides methods for detecting protein kinase activity using an assay particle described herein. In one aspect, a method involves contacting a sample containing a protein kinase with an assay particle, wherein the assay particle comprises a shell portion comprising an inorganic phosphor that is capable of binding selectively to phosphorylated molecules, and a protein kinase substrate comprising a moiety capable of emitting radiation, under conditions wherein the protein kinase can phosphorylate the substrate to produce a phosphorylated substrate, wherein binding of the phosphorylated substrate to the inorganic phosphor produces a light signal, and determining a protein kinase activity based on a level of detected phosphorylated substrate. In another aspect, a method for detecting protein kinase activity involves contacting a sample containing a protein kinase with an assay particle, wherein the assay particle comprises a coat portion comprising an inorganic phosphor that is capable of binding selectively to phosphorylated molecules, and a protein kinase substrate comprising a moiety capable of emitting radiation, under conditions wherein the protein kinase can phosphorylate the substrate to produce a phosphorylated substrate, wherein binding of the phosphorylated substrate to the inorganic phosphor produces a light signal, and determining a protein kinase activity based on a level of detected phosphorylated substrate. In another aspect, a method for detecting protein kinase activity involves contacting a sample containing a protein kinase with (i) an assay particle, wherein the assay particle comprises a coat portion comprising an inorganic phosphor and a binding agent selective for phosphorylated molecules, and is buoyant in aqueous media; and (ii) a protein kinase substrate comprising a moiety capable of emitting radiation, under conditions wherein the protein kinase can phosphorylate the substrate to produce a phosphorylated substrate, wherein binding of the phosphorylated substrate to the inorganic phosphor produces a light signal, and determining a protein kinase activity based on a level of detected phosphorylated substrate. Similar methods can be used for an assay particle that includes a core portion encased by a shell portion, and a coat portion covering the shell portion, wherein the shell portion comprises an inorganic phosphor and the coat portion comprises a target selective binding moiety, and wherein the assay particle is buoyant in aqueous media.

The invention provides methods for detecting protein phosphatase activity using an assay particle described herein. In one aspect, a method involves contacting a sample containing a protein phosphatase with an assay particle, wherein the assay particle comprises a shell portion comprising an inorganic phosphor that is capable of binding selectively to phosphorylated molecules and a protein phosphatase substrate comprising a moiety capable of emitting radiation is bound to the inorganic phosphor, under conditions wherein the protein phosphatase can dephosphorylate the substrate to produce a dephosphorylated substrate, wherein phosphorylated substrate bound to the inorganic phosphor produces a light signal, and determining a phosphatase activity based on a level of detected phosphorylated substrate. In another aspect, a method for detecting protein phosphatase activity involves contacting a sample containing a protein kinase with an assay particle, wherein the assay particle comprises a coat portion comprising an inorganic phosphor that is capable of binding selectively to phosphorylated molecules and wherein a protein phophatase substrate comprising a moiety that is capable of emitting radiation is bound to the inorganic phosphor, under conditions wherein the protein phosphatase can dephosphorylate the substrate to produce a dephosphorylated substrate, wherein phosphorylated substrate bound to the inorganic phosphor produces a light signal, and determining a phosphatase activity based on a level of detected phosphorylated substrate. In another aspect, a method for detecting protein phosphatase activity involves contacting a sample containing a protein phosphatase with an assay particle, wherein the assay particle comprises a coat portion comprising an inorganic phosphor and a binding agent selective for phosphorylated molecules, and wherein a protein phosphatase substrate comprising a moiety capable of emitting radiation is bound to the inorganic phosphor, under conditions wherein the protein phosphatase can dephosphorylate the substrate to produce a dephosphorylated substrate, wherein phosphorylated substrate bound to the inorganic phosphor produces a light signal, and determining a phosphatase activity based on a level of detected phosphorylated substrate. Similar methods can be used for an assay particle that includes a core portion encased by a shell portion, and a coat portion covering the shell portion, wherein the shell portion comprises an inorganic phosphor and the coat portion comprises a target selective binding moiety, and wherein the assay particle is buoyant in aqueous media.

The invention provides method for identifying a protein kinase modulator using an assay particle described herein. In one aspect, a method involves contacting a sample containing a protein kinase with (i) an assay particle comprising a shell portion comprising an inorganic phosphor that is capable of binding selectively to phosphorylated molecules; and (ii) a substrate comprising a moiety capable of emitting radiation, in the presence and absence of a candidate compound, under conditions wherein the protein kinase can phosphorylate the substrate to produce a phosphorylated substrate, wherein binding of the phosphorylated substrate to the inorganic phosphor produces a light signal; and detecting light signals produced in the presence and absence of the candidate compound, wherein a difference in light signals produced in the presence and absence of the compound identifies the compound as a protein kinase modulator. In another aspect, a method for identifying a protein kinase modulator involves contacting a sample containing a protein kinase with (i) an assay particle comprising a coat portion comprising an inorganic phosphor that is capable of binding selectively to phosphorylated molecules; and (ii) a substrate capable of emitting radiation, in the presence and absence of a candidate compound, under conditions wherein the protein kinase can phosphorylate the substrate to produce a phosphorylated substrate, wherein binding of the phosphorylated substrate to the inorganic phosphor produces a light signal; and detecting light signals produced in the presence and absence of the candidate compound, wherein a difference in light signals produced in the presence and absence of the compound identifies the compound as a protein kinase modulator. In another aspect, a method for identifying a protein kinase modulator involves contacting a sample containing a protein kinase with (i) an assay particle, wherein the assay particle comprises a coat portion comprising an inorganic phosphor and a binding agent selective for phosphorylated molecules; and (ii) a substrate comprising a moiety capable of emitting radiation, in the presence and absence of a candidate compound, under conditions wherein the protein kinase can phosphorylate the substrate to produce a phosphorylated substrate, wherein binding of the phosphorylated substrate to the inorganic phosphor produces a light signal; and detecting light signals produced in the presence and absence of the candidate compound, wherein a difference in light signals produced in the presence and absence of the compound identifies the compound as a protein kinase modulator. Similar methods can be used for an assay particle that includes a core portion encased by a shell portion, and a coat portion covering the shell portion, wherein the shell portion comprises an inorganic phosphor and the coat portion comprises a target selective binding moiety, and wherein the assay particle is buoyant in aqueous media. Similar methods can be used for an assay particle that includes a core portion encased by a shell portion, and a coat portion covering the shell portion, wherein the shell portion comprises an inorganic phosphor and the coat portion comprises a target selective binding moiety, and wherein the assay particle is buoyant in aqueous media.

The invention provides methods for identifying a cyclase modulator using an assay particle described herein. In one aspect, a method involves contacting a sample containing a cyclase with (i) an assay particle comprising a shell portion comprising an inorganic phosphor that is capable of binding selectively to non-cyclized nucleotides; and (ii) radioactively labeled non-cyclized nucleotide, in the presence and absence of a candidate compound, under conditions wherein the cyclase can acts on the substrate to produce a cyclized nucleotide, wherein binding of the non-cyclized nucleotide to the inorganic phosphor produces a light signal; and detecting light signals produced in the presence and absence of the candidate compound, wherein a difference in light signals produced in the presence and absence of the compound identifies the compound as a cyclase modulator. In another aspect a method for identifying a cyclase modulator involves contacting a sample containing a cyclase with (i) an assay particle comprising a coat portion comprising an inorganic phosphor that is capable of binding selectively to non-cyclized nucleotides; and (ii) radioactively labeled non-cyclized nucleotide, in the presence and absence of a candidate compound, under conditions wherein the cyclase can acts on the substrate to produce cyclized nucleotides, wherein binding of the non-cyclized nucleotide to the inorganic phosphor produces a light signal; and detecting light signals produced in the presence and absence of the candidate compound, wherein a difference in light signals produced in the presence and absence of the compound identifies the compound as a cyclase modulator. In another aspect, a method for identifying a cyclase modulator, comprising contacting a sample containing a cyclase with (i) an assay particle, wherein the assay particle comprises a coat portion comprising an inorganic phosphor and a binding agent selective for non-cyclized nucleotides; and (ii) radioactively labeled non-cyclized nucleotide, in the presence and absence of a candidate compound, under conditions wherein the cyclase can acts on the substrate to produce cyclized nucleotides, wherein binding of the non-cyclized nucleotide to the inorganic phosphor produces a light signal; and detecting light signals produced in the presence and absence of the candidate compound, wherein a difference in light signals produced in the presence and absence of the compound identifies the compound as a cyclase modulator. Similar methods can be used for an assay particle that includes a core portion encased by a shell portion, and a coat portion covering the shell portion, wherein the shell portion comprises an inorganic phosphor and the coat portion comprises a target selective binding moiety, and wherein the assay particle is buoyant in aqueous media.

The invention provides methods for identifying a phosphodiesterase modulator using an assay particle described herein. In one aspect, a method involves contacting a sample containing a phosphodiesterase with (i) an assay particle comprising a shell portion comprising an inorganic phosphor that is capable of binding selectively to non-cyclized nucleotides; and (ii) radioactively labeled cyclized nucleotide, in the presence and absence of a candidate compound, under conditions wherein the phosphodiesterase can acts on the substrate to produce non-cyclized nucleotides, wherein binding of the non-cyclized nucleotide to the inorganic phosphor produces a light signal; and detecting light signals produced in the presence and absence of the candidate compound, wherein a difference in light signals produced in the presence and absence of the compound identifies the compound as a phosphodiesterase modulator. In another aspect a method for identifying a phosphodiesterase modulator involves contacting a sample containing a phosphodiesterase with (i) an assay particle comprising a coat portion comprising an inorganic phosphor that is capable of binding selectively to non-cyclized nucleotides; and (ii) radioactively labeled cyclized nucleotide, in the presence and absence of a candidate compound, under conditions wherein the phosphodiesterase can acts on the substrate to produce non-cyclized nucleotides, wherein binding of the non-cyclized nucleotide to the inorganic phosphor produces a light signal; and detecting light signals produced in the presence and absence of the candidate compound, wherein a difference in light signals produced in the presence and absence of the compound identifies the compound as a phosphodiesterase modulator. In another aspect, a method for identifying a phosphodiesterase modulator involves contacting a sample containing a phosphodiesterase with (i) an assay particle, wherein the assay particle comprises a coat portion comprising an inorganic phosphor and a binding agent selective for non-cyclized nucleotides; and (ii) radioactively labeled cyclized nucleotide, in the presence and absence of a candidate compound, under conditions wherein the phosphodiesterase can acts on the substrate to produce non-cyclized nucleotides, wherein binding of the non-cyclized nucleotide to the inorganic phosphor produces a light signal; and detecting light signals produced in the presence and absence of the candidate compound, wherein a difference in light signals produced in the presence and absence of the compound identifies the compound as a phosphodiesterase modulator. Similar methods can be used for an assay particle that includes a core portion encased by a shell portion, and a coat portion covering the shell portion, wherein the shell portion comprises an inorganic phosphor and the coat portion comprises a target selective binding moiety, and wherein the assay particle is buoyant in aqueous media.

In some embodiments, the methods described herein involve use of a substrate for a protein kinase and a substrate for a phosphatase (that is, a phosphorylated substrate). Such substrates are well known to those skilled in the art and are commercially available for example, from ANASPEC, SIGMA, BIOMOL and others. In some embodiments, the methods described herein involve use of non-cyclized nucleotides. Procedures for tagging such molecules with radiation emitting labels such as radioactive and fluorescent labels are well known to those skilled in the art.

Examples of other analytes that can be assayed using the methods described herein include antigens, antibodies, hormones, metabolites, enzymes, proteins and drugs. Also, the assay format can be any of a variety of generally recognized assay types, including, for example, signal addition assays, in which a radiolabelled donor is added to an inactive substrate bound to the assay particle surface; signal removal assays, in which a radiolabeled substrate, already linked to the assay particle surface, is removed generally by the action of an enzyme, and product capture assays, in which the radiolabeled component, optionally in the presence of unlabelled sample component, is bound to the target selective binding agent, by means of a specific interaction between the component and the target selective binding agent on the surface of the assay particle. It is understood that an inorganic phosphor that binds selectively to a target molecule is a type of target selective binding agent.

The methods described herein can be used for screening candidate compounds for a modulator of an enzyme or a binding molecule. As used herein, the term "candidate compound" refers to any molecule that potentially acts as a modulator of a selected enzyme or binding partner of a selected molecule. A modulator can be determined to be, for example, an inhibitor, activator, agonist, antagonist or ligand using the screening methods disclosed herein. A candidate compound can be a naturally occurring macromolecule, such as a polypeptide, nucleic acid, carbohydrate, lipid, or any combination thereof. A candidate compound also can be a partially or completely synthetic derivative, analog or mimetic of such a macromolecule, or a small organic molecule prepared by combinatorial chemistry methods. If desired in a particular assay format, a candidate compound can be detectably labeled or attached to a solid support.

Methods for preparing libraries of compounds, including simple and complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., Curr. Opin. Chem. Biol. 2:422-428 (1998); Tietze et al., Curr. Biol., 2:363-371 (1998); Sofia, Mol. Divers. 3:75-94 (1998); Eichler et al., Med. Res. Rev. 15:481-496 (1995); and the like. Libraries containing large numbers of natural and synthetic compounds also can be obtained from commercial sources.

The number of different candidate compounds to test will depend on the application of the method. For example, one or a small number of candidate compounds are often used in manual screening procedures, or when it is desired to compare efficacy among several predicted ligands, agonists or antagonists. However, it is generally understood that the larger the number of candidate compounds, the greater the likelihood of identifying a compound having the desired activity in a screening assay. Additionally, large numbers of compounds can be processed in high-throughput automated screening assays. More than one compound can be screened in a sample, if desired. Screening of compounds also can be performed by single compound assays run in parallel.

The technology herein provides a kit containing an assay particle described herein. The kit also can contain a substrate for an enzyme which is labeled to be capable of emitting radiation. Examples of such kits include kits for assaying a kinase, phosphatase, and cyclase. A kit provided by the invention can contain a variety of components in addition to assay particles. A package can contain, for example, instructions for using a assay particles, a recommendation regarding the concentration of sample for use in a particular application, as well as guidance regarding temperature, buffer conditions and incubation time periods. A kit can optionally can contain other components, such as one or more of standards, substrates, target selective binding agents, coating materials, and assay particles to receive preparation by the user prior to beginning an assay. Those skilled in the art will be able to select suitable components for inclusion in a kit or other commercial package of the invention based on such exemplary factors as design of the assay protocol, the particular inorganic phosphor and radiation emitting component used for performing an assay, method of detection or measurement to be employed once the assay has been performed, consumer price point, shipping and handling suitability and the like.

A kit provided by the technology described herein can include a core portion encased by a shell portion, wherein the shell portion comprises an inorganic phosphor that binds selectively to a target molecule, and an enzyme substrate comprising a moiety capable of emitting radiation.

In another aspect, a kit provided by the technology described herein can include assay particle, comprising a core portion encased by a shell portion, and a coat portion covering the shell portion, wherein the coat portion comprises an inorganic phosphor that binds selectively to a target molecule, and an enzyme substrate capable of emitting radiation.

In a further aspect a kit provided by the technology described herein can include assay particle, comprising a core portion encased by a shell portion, and a coat portion covering the shell portion, wherein the coat portion comprises an inorganic phosphor and a target selective binding moiety, and wherein the assay particle is buoyant in aqueous media, and an enzyme substrate capable of emitting radiation.

In yet another aspect, a kit provided by the technology described herein can include an assay particle, comprising a core portion encased by a shell portion, and a coat portion covering the shell portion, wherein the shell portion comprises an inorganic phosphor and the coat portion comprises a target selective binding moiety, and wherein the assay particle is buoyant in aqueous media, and an enzyme substrate capable of emitting radiation.

Although specific embodiments have been illustrated and described herein, it will be appreciated by those skilled in the art that any arrangement which is calculated to achieve the same purpose may be substituted for the specific embodiments shown. This application is intended to cover any adaptations or variations of the present invention.

A kit can be prepared for assayed any of a variety of anaytes, enzymes and molecular interactions. Examples of specific kits include kits for assaying a protein kinase, which can include assay particles that bind selectively to phosphorylated molecules and a kinase substrate that is radioactively or fluorescently labeled, for example, a tritium-labeled peptide substrate; kits for assaying a protein phosphatase, which can include assay particles that bind selectively to phosphorylated molecules and a phosphatase substrate that is radioactively or fluorescently labeled; kits for assaying a cyclase, which can include assay particles that bind selectively to non-cyclized nucleotides, such as AMP and GMP, and non-cyclized nucleotides that are radioactively labeled; and kits for assaying a phosphodiesterase, which can include assay particles that bind selectively to non-cyclized nucleotides, such as AMP and GMP, and cyclized nucleotides that are radioactively labeled.

REFERENCES

Bertoglio-Matte J H Immediate ligand detection assay. U.S. Pat. No. 4,568,649, Feb. 4, 1986.

Brandish P E, Hill L A, Zheng W, Scolnick E M. Scintillation proximity assay of inositol phosphates in cell extracts: high-throughput measurement of G-protein-coupled receptor activation. Anal Biochem. 2003, 313(2): 311-8.

Bryant R, McGuinness D, Turek-Etienne T, Guyer D, Yu L, Howells L, Caravano J, Zhai Y, Lachowicz J. WGA-coated yttrium oxide beads enable an imaging-based adenosine 2a receptor binding scintillation proximity assay suitable for high throughput screening. Assay Drug Dev Technol. 2004; 2(3):290-9.

Caruso, R A Nanocasting and Nanocoating. Top Curr Chem. 2003, 226:91-118.

Caruso F. Hollow inorganic capsules via colloid-templated layer-by-layer electrostatic assembly. Top Curr Chem. 2003, 227: 145-168.

Niesen, T P, De Guire, M R Review: Deposition of ceramic thin films at low temperatures from aqueous solutions. J. Electroceram. 2001, 6: 169-207

Onda K, Li B, Zhao J, Jordan K D, Yang J, Petek H. Wet electrons at the H2O/TiO2 (110) surface. Science. 2005; 308 (5725):1154-1158.

Larsen M R, Thingholm T E, Jensen O N, Roepstorff P, Jorgensen T J. Highly selective enrichment of phosphorylated peptides from peptide mixtures using titanium dioxide microcolumns. Mol Cell Proteomics. 2005 Apr. 27; [Epub ahead of print]

Jessop, R. A. Scintillation proximity test. U.S. Pat. No. 6,524,786 B1 Feb. 25, 2003.

Thomson, J., ter Wiel, J., van Lune, H., Bosel, H M, Kremer, G H Scintillation counting system using scintillator capsules. U.S. Pat. No. 5,512,753 Apr. 30, 1996.

Normant E. Melendez A, Casamitjana O., and Moreau F Methods and compositions for screening modulators of lipid kinases. United States Patent Application Publication No. US 2002/0042091 A1, Apr. 11, 2002.

Brandish P E, Hill L A Assays for inositol phosphates. United States Patent Application Publication US 2004/0180394 A1, Sep. 16, 2004.

Boge A., Lavis, L D, Sportsman, R., Hoekstra, M F, and Huang, W. Molecular modification assays. United States Patent Application Publication No. 2004/024586 A1, Dec. 9, 2004.

Potter, C., Warner, G., Oikari, T. Method for simultaneous assay of ligands. U.S. Pat. No. 5,246,869, Sep. 21, 1993.

EXAMPLES

Example 1

This example describes preparation of assay particles based on hollow glass microspheres.

Two types of hollow glass microspheres (glass bubbles) (S60 10,000 and S60 HS, 3M Corporation) were used for preparing assay particles. Both types of bubbles were received as powdery samples and were evaluated in parallel. About 2.5 g of bubbles were resuspended in 40 ml of water in a 50 ml conical centrifuge tube and centrifuged at 2 kRPM for 5 min. Most of the glass bubbles floated as expected (bubble density is about 0.6 g/cc) forming a "creamy" thick layer on the top. A small fraction of bubbles sunk to the bottom of the tube. About 1 ml of the bubbles floating on the top was pipetted out and 6 ml of the 50 mM TiF4 solution was added for coating the surfaces with $TiO_2$. The $TiF_4$ was prepared as follows: weighing 0.31 g of Ti (IV) fluoride (Sigma-Aldrich catalog #333239) in container with cap (455 Filter Unit Receiver); adding 20 ml of deionized water (Milli-Q) and closing the cap right away to avoid escape of hydrofluoric acid from the container. It takes about 30-40 min. to completely dissolve the Titanium fluoride. Then, 25 ml of 0.1% Ammonium Hydroxide was added, and the pH was adjusted to 1.8 by adding 1-2 drops of 1% NH4OH. The negative control of uncoated beads was prepared in a similar way using water instead of $TiF_4$ solution. Following the 2 hour coating at 60° C., the bubbles were centrifuged and the top layer of the floating bubbles was collected and diluted in 40 ml of water.

This example shows successful coating of glass bubbles with $TiO_2$. Most of the glass bubbles remained afloat after the $TiO_2$-coating.

Example 2

Figure 2A:
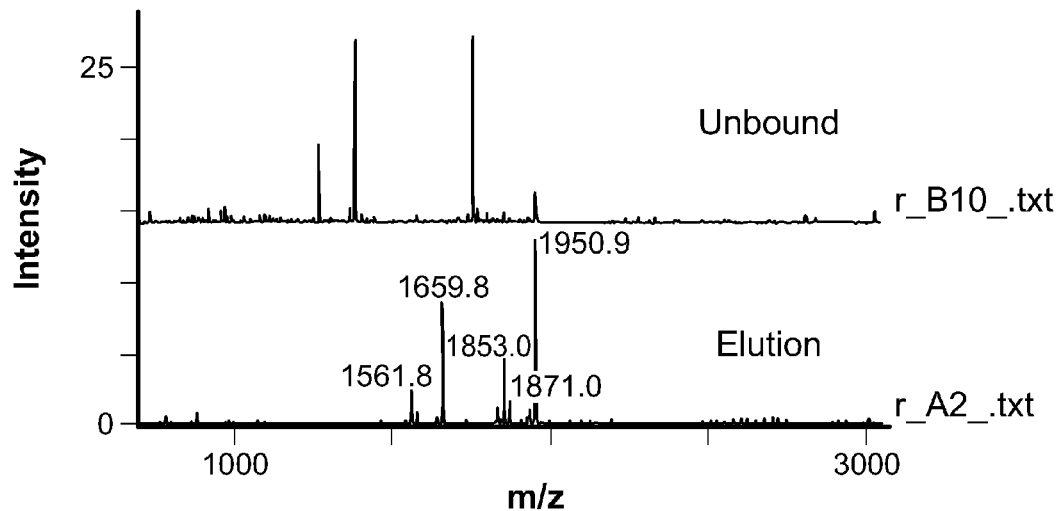
FIG. 2 shows results from experiments in which $TiO_2$-coated assay particles were used to prepare a sample enriched in phosphorylated molecules. Shown in FIG. 2A are mass spectra of eluted and unbound samples of α-casein tryptic digest fractionated on $TiO_2$-coated magnetic beads. Shown in FIG. 2B are mass spectra of eluted, and unbound and control samples of α-casein tryptic digest fractionated on $TiO_2$-coated glass assay particles as well as the negative control mass spectrum of α-casein tryptic digest eluted from uncoated glass assay particles.
Figure 2B:
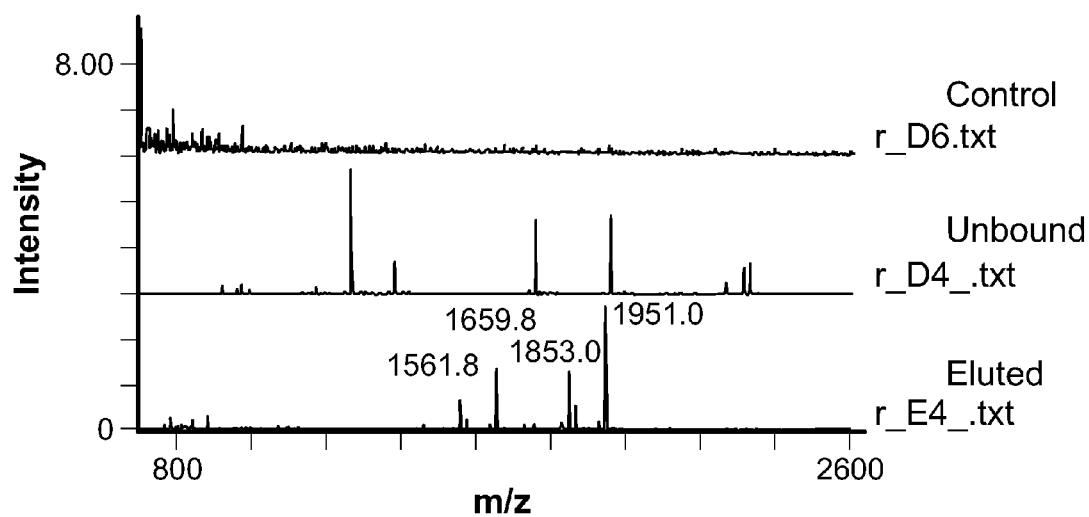

This example describes enrichment of phosphorylated peptides using glass assay particles coated with titanium dioxide Using vigorous mixing, the 200 µl, 100 µl, and 50 µl of bubble suspension, either uncoated or prepared as described in Example 1, was dispensed into a MULTISCREEN plate (Millipore). Two columns, 8 wells per column, were dispensed for each volume of bead suspension and for each type of beads. The uncoated beads were dispensed at 200 µl/well in a FIG. 2 shows that successful enrichment of phosphopeptides was achieved for the α-casein tryptic digest fractionation. The S60 10,000 and S60 HS glass bubbles performed similarly in these experiments. Uncoated beads, on the other hand yielded low levels of nonselective binding of peptides from the trypic digest.

This example shows selective enrichment of phosphopeptides from an α-casein tryptic digest using $TiO_2$-coated glass bubbles.

Example 3

This example describes a method for performing SPA-based protein kinase detection using an assay particle of the invention. $^3$H-labeled Abl and glycogen synthase 1-10 peptide are obtained. Abl peptide is a substrate for Abl tyrosine kinase and its amino acid sequence is E-A-I-Y-A-A-P-F-A-K-K-K (MW 1336) (SEQ ID NO:1). Glycogen synthase 1-10 peptide is a substrate for Calcium-Calmodulin-Dependent protein Kinase II and its amino acid sequence is P-L-S-R-T-L-S-V-S-S (MW 1045.2) (SEQ ID NO:2). The peptides are applied individually to various wells of a 96-well microplate, generally at a concentration of 0.01 to 10 µM. The assay is performed in any appropriate support or device, including plate, tube, flask or vial. Multi-well plates allow multiple assays to be performed in parallel. Next, kinase reactions are performed, for example, in a 30 to 100 µL reaction volume containing 20,000 U/mL or 1600 units enzyme (Calmodulin-Dependent protein Kinase II, New England Biolabs, Beverly, Mass.). Alternatively, the enzyme is obtained from a eukaryotic cell lysate comprising 0.1 to 50 µg of total proteins. The kinase reaction is performed using buffer, $CaCl_2$, calmodulin, and ATP supplied with the enzyme. The supplied kinase buffer includes 50 mM Tris-HCl, 10 mM $MgCl_2$, 2 mM dithiothreitol, 0.1 mM $Na_2EDTA$, pH 7.5. $CaCl_2$, calmodulin and ATP (working concentrations range from 2 mM to 1.2 µM). Typically, the amount of kinase employed in the assay should is be sufficient to modify less than one third of the tritiated substrate during a defined incubation period. The reaction solution with enzyme is pipetted into the well and incubated at 37 degrees centigrade for up to three hours, optionally with mixing supplied by an orbital shaker. After incubation, assay particles containing an inorganic phosphor thin film coating are added to the reaction mixture. Europium-doped yttrium oxide, europium-doped zirconia or europium-doped yttrium aluminum garnet are examples of inorganic phosphors that serve both as a target selective binding agent for phosphorylated peptides and as a scintillant. The assay particles are optionally suspended in 0 to 70% glycerol. After further incubation for a period of 10 minutes to 24 hours, the amount or quantity of particle-bound phosphopeptide is assessed by scintillation counting or scintillation imaging, using either a TopCount-HTS, 12 Detector, 96/384 instrument or ViewLux™ ultraHTS Microplate Imager (PerkinElmer, Boston, Mass.), respectively. Calmodulin-dependent kinase II specifically phosphorylates the glycogen synthase 1-10 peptide, leading to detectable scintillations, while the Abl peptide is not phosphorylated and thus does not activate the inorganic phosphor-coated particles. Though illustrated with descriptions relating to the detection of phosphorylated molecules using SPA, applications of the method and materials are not restricted to any particular analyte, class of substances, or binding component reactant pair and in principle any binding assay can be performed according to a method of the invention.

What is claimed is:

1. A method for detecting protein kinase activity, the method comprising:
   contacting a sample suspected of containing a protein kinase with:
   (i) an assay particle, wherein the assay particle comprises:
      a core portion encased by a shell portion; and
      a coat portion covering the shell portion,
         wherein the shell portion of the assay particle comprises titanium dioxide and a material selected from the group consisting of glass, ceramic, and combinations thereof;
         wherein the coat portion comprises titanium dioxide and a target selective binding agent; and
         wherein the assay particle is hollow and is buoyant in aqueous media; and
   (ii) a protein kinase substrate comprising a moiety capable of emitting radiation under conditions wherein the protein kinase can phosphorylate the substrate to produce a phosphorylated substrate;
      wherein binding of the phosphorylated substrate to titanium dioxide produces a light signal; and
   determining a protein kinase activity based on a level of detected light signal.

2. The method of claim 1, wherein the core portion comprises a gas selected from the group consisting of air, nitrogen, oxygen, and combinations thereof.

3. The method of claim 1, wherein the assay particle has a density of less than 1 g/cm$^3$.

4. The method of claim 1, wherein the shell portion of the assay particle comprises glass.

5. The method of claim 1, wherein the shell portion of the assay particle comprises ceramic.

6. The method of claim 1, wherein the core portion comprises air.

7. The method of claim 1, wherein the core portion comprises nitrogen.

8. The method of claim 1, wherein the core portion comprises oxygen.

9. The method of claim 1, wherein the target selective binding agent is selected from the group consisting of an antibody, aptamer, protein A, protein G, streptavidin, avidin, captavidin, neutravidin, metal chelate, siderophore, lectin, and oligonucleotide.

10. The method of claim 1, wherein the coat portion has a thickness of less than 3000 μm.

11. The method of claim 1, wherein the coat portion has a thickness of less than 2000 μm.

12. The method of claim 1, wherein the coat portion has a thickness of less than 1000 μm.

13. The method of claim 1, wherein the shell portion of the assay particle comprises a target selective binding agent.

14. The method of claim 13, wherein the target selective binding agent is selected from the group consisting of an antibody, aptamer, protein A, protein G, streptavidin, avidin, captavidin, neutravidin, metal chelate, siderophore, lectin, and oligonucleotide.

15. The method of claim 1, wherein the shell portion of the assay particle has a thickness of about 1 mm to about 500 mm.

16. The method of claim 1, wherein the shell portion of the assay particle has a thickness of about 1 mm to about 200 mm.

17. The method of claim 1, wherein the assay particle comprises an outer layer covering the coat portion.

18. The method of claim 17, wherein the outer layer comprises a target selective binding agent.

19. The method of claim 18, wherein the target selective binding agent is selected from the group consisting of an antibody, aptamer, protein A, protein G, streptavidin, avidin, captavidin, neutravidin, metal chelate, siderophore, lectin, and oligonucleotide.

20. The method of claim 1, wherein the assay particle comprises an encoding element.

21. The method of claim 20, wherein the encoding element comprises a radio frequency identifier, holographic identifier, fluorophore, or quantum dot.

22. A method for detecting protein kinase activity, the method comprising:

contacting a sample suspected of containing a protein kinase with:
(i) an assay particle, wherein the assay particle comprises:
a core portion encased by a shell portion; and
a coat portion covering the shell portion,
wherein the shell portion of the assay particle comprises a target selective binding agent and a material selected from the group consisting of glass, ceramic, and combinations thereof;
wherein the coat portion comprises titanium dioxide and a target selective binding agent; and
wherein the assay particle is hollow and is buoyant in aqueous media; and
(ii) a protein kinase substrate comprising a moiety capable of emitting radiation under conditions wherein the protein kinase can phosphorylate the substrate to produce a phosphorylated substrate;
wherein binding of the phosphorylated substrate to titanium dioxide produces a light signal; and
determining a protein kinase activity based on a level of detected light signal.

23. The method of claim 22, wherein the core portion comprises a gas selected from the group consisting of air, nitrogen, oxygen, and combinations thereof.

24. The method of claim 22, wherein the assay particle has a density of less than 1 g/cm$^3$.

25. The method of claim 22, wherein the shell portion of the assay particle comprises glass.

26. The method of claim 22, wherein the shell portion of the assay particle comprises ceramic.

27. The method of claim 22, wherein the core portion comprises air.

28. The method of claim 22, wherein the core portion comprises nitrogen.

29. The method of claim 22, wherein the core portion comprises oxygen.

30. The method of claim 22, wherein the target selective binding agent is selected from the group consisting of an antibody, aptamer, protein A, protein G, streptavidin, avidin, captavidin, neutravidin, metal chelate, siderophore, lectin, and oligonucleotide.

31. The method of claim 22, wherein the coat portion has a thickness of less than 3000 μm.

32. The method of claim 22, wherein the coat portion has a thickness of less than 2000 μm.

33. The method of claim 22, wherein the coat portion has a thickness of less than 1000 μm.

34. The method of claim 22, wherein the shell portion of the assay particle comprises titanium dioxide.

35. The method of claim 22, wherein the target selective binding agent is selected from the group consisting of an antibody, aptamer, protein A, protein G, streptavidin, avidin, captavidin, neutravidin, metal chelate, siderophore, lectin, and oligonucleotide.

36. The method of claim 22, wherein the shell portion of the assay particle has a thickness of about 1 mm to about 500 mm.

37. The method of claim 22, wherein the shell portion of the assay particle has a thickness of about 1 mm to about 200 mm.

38. The method of claim 22, wherein the assay particle comprises an outer layer covering the coat portion.

39. The method of claim 38, wherein the outer layer comprises a target selective binding agent.

40. The method of claim 39, wherein the target selective binding agent is selected from the group consisting of an antibody, aptamer, protein A, protein G, streptavidin, avidin, captavidin, neutravidin, metal chelate, siderophore, lectin, and oligonucleotide.

41. The method of claim 22, wherein the assay particle comprises an encoding element.

42. The method of claim 41, wherein the encoding element comprises a radio frequency identifier, holographic identifier, fluorophore, or quantum dot.

43. A method for detecting protein kinase activity, the method comprising:
contacting a sample suspected of containing a protein kinase with:
(i) an assay particle, wherein the assay particle comprises:
a core portion encased by a shell portion; and
a coat portion covering the shell portion,
wherein the shell portion of the assay particle comprises a material selected from the group consisting of glass, ceramic, and combinations thereof, and wherein the shell portion of the assay particle has a thickness of about 1 mm to about 500 mm;
wherein the coat portion comprises titanium dioxide and a target selective binding agent; and
wherein the assay particle is hollow and is buoyant in aqueous media; and
(ii) a protein kinase substrate comprising a moiety capable of emitting radiation under conditions wherein the protein kinase can phosphorylate the substrate to produce a phosphorylated substrate;
wherein binding of the phosphorylated substrate to titanium dioxide produces a light signal; and
determining a protein kinase activity based on a level of detected light signal.

44. The method of claim 43, wherein the core portion comprises a gas selected from the group consisting of air, nitrogen, oxygen, and combinations thereof.

45. The method of claim 43, wherein the assay particle has a density of less than 1 g/cm$^3$.

46. The method of claim 43, wherein the shell portion of the assay particle comprises glass.

47. The method of claim 43, wherein the shell portion of the assay particle comprises ceramic.

48. The method of claim 43, wherein the core portion comprises air.

49. The method of claim 43, wherein the core portion comprises nitrogen.

50. The method of claim 43, wherein the core portion comprises oxygen.

51. The method of claim 43, wherein the target selective binding agent is selected from the group consisting of an antibody, aptamer, protein A, protein G, streptavidin, avidin, captavidin, neutravidin, metal chelate, siderophore, lectin, and oligonucleotide.

52. The method of claim 43, wherein the shell portion of the assay particle comprises titanium dioxide.

53. The method of claim 43, wherein the shell portion of the assay particle comprises a target selective binding agent.

54. The method of claim 53, wherein the target selective binding agent is selected from the group consisting of an antibody, aptamer, protein A, protein G, streptavidin, avidin, captavidin, neutravidin, metal chelate, siderophore, lectin, and oligonucleotide.

55. The method of claim 43, wherein the shell portion of the assay particle has a thickness of about 1 mm to about 200 mm.

56. The method of claim 43, wherein the assay particle comprises an outer layer covering the coat portion.

57. The method of claim 56, wherein the outer layer comprises a target selective binding agent.

58. The method of claim 57, wherein the target selective binding agent is selected from the group consisting of an antibody, aptamer, protein A, protein G, streptavidin, avidin, captavidin, neutravidin, metal chelate, siderophore, lectin, and oligonucleotide.

59. The method of claim 43, wherein the assay particle comprises an encoding element.

60. The method of claim 59, wherein the encoding element comprises a radio frequency identifier, holographic identifier, fluorophore, or quantum dot.

* * * * *